United States Patent [19]

Braughler et al.

[11] Patent Number: 4,554,271

[45] Date of Patent: Nov. 19, 1985

[54] USE OF HIGH DOSES OF DERIVATIVES OF 6α-METHYLPREDNISOLONE FOR THE ACUTE TREATMENT OF STROKE SYNDROME

[75] Inventors: J. Mark Braughler, Kalamazoo; Edward D. Hall, Portage, both of Mich.

[73] Assignee: The Upjohn Company, Kalamazoo, Mich.

[21] Appl. No.: 582,987

[22] Filed: Feb. 24, 1984

[51] Int. Cl.⁴ .............................................. A61K 31/56
[52] U.S. Cl. .................................................... 514/179
[58] Field of Search ......................... 424/243; 514/179

[56] References Cited

U.S. PATENT DOCUMENTS

| | | | |
|---|---|---|---|
| 2,897,218 | 7/1959 | Sebek et al. | 260/397.45 |
| 4,302,452 | 11/1981 | Pittman, Jr. | 424/243 |
| 4,343,799 | 8/1982 | Heckler | 424/243 |
| 4,448,774 | 5/1984 | Clemente et al. | 424/243 |

OTHER PUBLICATIONS

Federation Proceedings, vol. 42, (1983), p. 1367, Abstract 6297.
Hall, E. D. & Braughler, J. M., Glucocorticoid Mechanisms in Acute Spinal Cord Injury, Surg. Neurol., 18: 320–327, (1982).
Hall, E. D. & Braughler, J. M., Correlation of Methylprednisolone Levels . . . , J. Neurosurg., 56: 838–844, (1982).
Hall, E. D. & Braughler, J. M., Effects of Intravenous Methylprednisolone in Spinal Cord . . . , J. Neurosurg., 57: 247–253, (1982).
Jarrott, D. M., et al., A Gerbil Model of Cerebral Ischemia . . . , Stroke, 11: 203–209, (1980).
Palmer, G. C., Therapeutic Protection of Adenylate Cyclase Systems . . . , Fed. Proc., 42: 1367, (1983).

*Primary Examiner*—Elbert L. Roberts
*Attorney, Agent, or Firm*—William G. Jameson

[57] ABSTRACT

Use of water soluble 21-dibasic esters of 1-dehydro-6α-methylhydrocortisone for the acute treatment of stroke syndrome in humans.

5 Claims, No Drawings

USE OF HIGH DOSES OF DERIVATIVES OF 6α-METHYLPREDNISOLONE FOR THE ACUTE TREATMENT OF STROKE SYNDROME

BACKGROUND OF THE INVENTION

1. Field of the Invention

This invention relates to a method of using high doses of water soluble 21-dibasic esters of 1-dehydro-6α-methylhydrocortisone for the acute treatment of stroke syndrome in humans, a condition with sudden onset caused by acute vascular lesions of the brain, such as hemorrhage, embolism, thrombosis, or rupturing aneurysm, which may be marked by hemiplegia or hemiparesis, vertigo, numbness, aphasia, and dysarthria; it is often followed by permanent neurologic damage.

Stroke syndrome is also commonly known as stroke, cerebrovascular accident and CVA.

2. Description of the Prior Art

1-Dehydro-6α-methylhydrocortisone (6α-methylprednisolone) is a known pharmaceutical for treating inflammation.

Water soluble 21-polybasic esters of 1-dehydro-6α-methylhydrocortisone, their salts and methods for preparing them are described in U.S. Pat. No. 2,897,218.

The use of high doses of methylprednisolone in the treatment of acute spinal cord injury has been previously disclosed. See E. D. Hall and J. M. Braughler, Glucocorticoid Mechanisms in Acute Spinal Cord Injury: A Review and Therapeutic Rationale, Surg. Neurol., 18; 320–327 (1982):

ABSTRACT

This review seeks to provide pharmacological evidence that incensive glucocorticoid dosing can enhance sensorimotor recovery after blunt spinal cord trauma. It is suggested that high doses of glucocorticoids can beneficially effect the injured cord through the influence of at least three mechanisms. These are: (1) a facilitation of neuronal excitability and impulse conduction; (2) an improved blood flow; and, perhaps most importantly, (3) the preservation of cord ultrastructure through a reduction of injury-induced, free radical-catalyzed lipid peroxidation. In the case of methylprednisolone, the minimal intravenous dosage required to initially achieve each of these effects is in the range of 15 to 30 mg per kilogram of body weight, which is beyond that used currently for neurosurgical purposes. In addition, based upon the hypothesized mechanism of action and the tissue pharmacokinetics, the earliest possible initiation of therapy is imperative and rigorous maintenance dosing for an as yet undetermined length of time is needed.

; and

J. M. Braughler and E. D. Hall, Correlation of Methylprednisolon levels in cat spinal cord with its effects on $(Na^+ + K^+)$-ATPase, lipid peroxidation, and alpha motor neuron function, J. Neurosurg., 56; 838–844 (1982):

ABSTRACT

Large intravenous doses of methylprednisolone sodium succinate are associated with biochemical and electrophysiological effects in the cat spinal cord which may be of therapeutic value in the treatment of spinal cord injury. The potentially beneficial effects of large doses of the glucocorticoid include: 1) an enhancement of spinal cord $(Na^+ + K^+)$-ATPase activity; 2) an attenuation of lipid peroxide formation; 3) a hyperpolarization of motor neuron resting membrane potentials; and 4) an accelerated impulse conduction along the myelinated portion of the motor axon. Each of these is apparent with spinal cord tissue levels of methylprednisolone around 1.3 $\mu g/gm$ wet weights, which are rapidly obtained following a single intravenous dose of 30 mg/kg. The half-life of methylprednisolone in cat spinal cord following a single intravenous administration, as well as the duration of its pharmacological actions, is roughly 3 hours. The data suggest that, in order to be of therapeutic value in the treatment of acute spinal cord trauma, early intervention with high-dose intravenous methylprednisolone (30 to 40 mg/kg) is necessary, followed by intravenous maintenance dosing of 15 to 20 mg/kg every 2 to 3 hours. The rationale and duration for this regimen are discussed.

; and

E. D. Hall and J. M. Braughler, Effects of intravenous Methylprednisolone on spinal cord lipid peroxidation and $(Na^+ + K^+)$-ATPase activity, J. Neurosurg., 57: 247–253 (1982):

ABSTRACT

The present study was undertaken to examine the ability of a single large intravenous dose of methylprednisolone (15, 30, or 60 mg/kg) to attenuate lipid peroxidation and enhance $(Na^+ + K^+)$-ATPase activity during the 1st hour after a 400 gm-cm injury to the cat spinal cord. The contusion injury was associated with a rise in the concentration of fluorescent lipid peroxy products in the injured segment at 1 hour. In addition, the accumulation of cyclic guanosine 3',5'-monophosphate (cyclic GMP), which was used as a new index of injury-induced free radical reactions, in the injured spinal segment was twice control levels. The injury-induced increase in fluorescence and cyclic GMP content in the confused spinal segment at 1 hour was completely prevented by the administration of 15 or 30 mg/kg of methylprednisolone at 30 minutes after injury. A 60-mg/kg dose, however, did not prevent the elevation in cyclic GMP. A concomitant examination of the acute effects of glucocorticoid administration on $(Na^+ + K^+)$-ATPase activity in the injured cord revealed a striking increase of enzyme activity after the 30-mg/kg dose, but a depression in activity with the 60-mg/kg dose. These results demonstrate that a single massive dose of methylprednisolone can beneficially reduce free-radical reactions and lipid peroxidation as well as enhance the activity of neuronal $(Na^+ + K^+)$-ATPase during the early phase after spinal cord contusion. The requirement for doses to be in the range of 15 to 30 mg/kg in order to produce these neurochemical changes is consistent with other studies that have demonstrated significantly greater recovery and tissue preservation in spinal cord-injured animals treated with comparable doses of methylprednisolone soon after injury. These findings suggest the need for a rigorous approach to glucocorticoid therapy in central nervous system trauma.

; and

E. D. Hall and J. M. Braughler, Acute effects on intravenous glucocorticoid pretreatment on the in vitro peroxidation of cat spinal cord tissue, Expt. Neurol., 73, 321-324 (1981); H. B. Demopoulos, et al., Further studies on free-radical pathology in the major central nervous system disorders: Effect of very high doses of methylprednisolone on the functional outcome, morphology, and chemistry of experimental spinal cord impact injury. Can. J. Physiol. Pharmacol., 60, 1415-24 (1982); W. Young, et at., Effect of high-dose corticosteroid therapy on blood flow, evoked potentials, and extracellular calcium in experimental spinal injury, J. Neurosurg, 57, 667-73 (1982); B. A. Green, et al., A comparative study of steroid therapy in acute experimental spinal cord injury, Surg. Neurol., 13, 91-97 (1980).

The use of high doses of methylprednisolone in hermorrhagic and septic shock, acute respiratory distress syndrome (ARDS), and head injury (trauma) is also known. See Pathophysiology of Shock, Anorexia and Ischemia, R. A. Cowley and B. F. Trump, eds., 1982, pp. 393, 465-478, 491 and 606.

The evaluation of cerebral ischemia in gerbils is well known. See for example: M. Simalek, et al., The therapeutic effect on experimental cerebral ischemia in Mongolian gerbils, Cerebral Vascular Disease, J. S. Meyer, editor, pp. 186-92 (1979); S. Levine, et al., Cerebral ischemia in infant and adult gerbils, Arch. Pathol., 87, 315-317 (1969); A. J. Kastin, et al., Failure of MIF-1 or naloxone to reverse ischemia-induced neurological deficits in gerbils, Pharmacol. Biochem Behav., 17, 1083-1085 (1982).

D. M. Jarrott, et al., A gerbil model of cerebral ischemia suitable for drug evaluation, Stroke, 11: 203-209 (1980), disclosed that methylprednisolone 35 mg/kg improved survival of an anesthetized gerbil after cerebral ischemia produced by bilateral occlusion of the carotid arteries.

R. K. Laha, et al., Protective effects of methylprednisolone and DMSO in experimental middle cerebral artery embolectomy, J. Neurosurg., 49, 508-516 (1978) reported in the abstract that:

Acute arterial embolism continues to be a major cause of stroke morbidity in children and young adults. Potential therapy modalities include medical management and/or cerebral revascularization. The canine middle cerebral artery (MCA) was embolized by means of a pliable cylinder, 8 mm long by 1.6 mm in diameter, via the internal carotid artery. Control and experimental embolectomies were performed 6 hours following embolization. The experimental animals were treated with either dimethyl sulfoxide (DMSO) or methyl prednisolone. In the control animals, the average area of infarction in the brain was 1.45 cu cm. The animals treated with methyl prednisolone (2 mg/kg) or DMSO (2 gm/kg) showed no infarction of the brain, whereas methyl prednisolone (30 mg/kg) did not prevent infarction.

and noted at page 514 that:

Conflicting effects of steroids in acute stroke have also been reported in clinical trials. A favorable response was noted by Russek, et al.,[49] and Patten, et al.,[44] while others have found disappointing results.[5,8,39] However, methyl prednisolone has been effective in relieving cardiac, renal, and hepatic ischemia,[7] ...

J. Lozman, et al., Cardiopulmonary adjustments following single high dosage administration of methylprednisolone in traumatized man, Ann. Surg., 181, 317-324 (1975) reported the effects of a single 30 mg/kg dose in ten seriously ill patients, seven were victims of multiple trauma accidents, one was in septic shock following surgery, and two patients were postoperative following repair of ruptured adominal aneurysms.

3. Description of Other Art

G. C. Palmer, Therapeutic protection of adenylate cyclase systems following bilateral stroke in gerbils, Fed. Proc., 42, 1367 (1983), disclosed that if the barbiturate anesthetized animals were pretreated with methylprednisolone (30 mg/kg, 30 min.) prior to carotid ligation, the damaging effect of 60 minutes occlusion plus 15 minutes recirculation was prevented and that, in preliminary work, methylprednisolone prevented chronic (7 days) enzyme damage elicited by 15 minutes of bilateral stroke. A subsequent report indicated that:

Synthetic Steroid May Help Stroke Victims

Methylprednisolone, a synthetic steroid, may be useful in preventing the aftermath of stroke, a reaction that can cause serious brain damage. Dr. Gene C. Palmer of Frist-Massey Neurological Institute, Nashville, has reported that methylprednisolone prevented damage to a brain biochemical system being studied in gerbils. The drug, which is a potent anti-inflammatory agent, prevented brain edema when given to the gerbils before stroke was induced. Stroke is a second leading cause of death and the major cause of disability in the United States. One of the big problems in treating stroke patients lies in the aftermath of stroke.

However, no dosage or regimen of administration to humans was disclosed.

M. B. Bracken, et al., Efficacy of methylprednisolone in acute spinal cord injury, JAMA, Jan. 6, 1984, 251, No. 1, 45-52, described a multicenter trial to examine the efficacy of a high dose of methylprednisolone (1000 mg bolus and daily thereafter for ten days) compared with a standard dose (100 mg bolus and daily thereafter for ten days) and noted it is possible the high dose did not reach therapeutic levels since animal studies suggest that methylprednisolone in the range of 15 to 30 mg/kg of body weight is necessary to improve neuronal excitability, increase postinjury blood flow, and preserve cord ultrastructure by reducing injury-induced, free radial-catalyzed lipid peroxidation.

The applicants made a presentation to members of New York University, Neurosurgery Department on Mar. 15, 1983 and recommended a regimen of treatment with methylprednisolone for the treatment of acute spinal cord injury of about 30 mg/kg administered intravenously as soon as possible after injury, followed by a 15 mg/kg dose intravenously two hours later and continuing 15 mg/kg intravenous doses every six hours thereafter for three days.

The applicants recently published two additional papers: J. Mark Braughler and Edward D. Hall, Lactate and pyruvate metabolism in injured cat spinal cord before and after a single large intravenous dose of methylprednisolone, J. Neurosurg., 59, 256–261, (August 1983); and Uptake and elimination of methylprednisolone from contused cat spinal cord following intravenous injection of the sodium succinate ester, J. Neurosurg., 58, 538–542, (April , 1983); and described in the latter:

> The acutely traumatized spinal cord may fortuitously be able to concentrate glucocorticoid where it is needed most, in the injured tissue. It is clear, however, that the early initiation of glucocorticoid therapy provides the best chance for tissue uptake of the drug. Our earlier studies, showing that a 15- or 30-mg/kg intravenous dose given 30 minutes after trauma can significantly reduce lipid peroxidation and enhance $(Na^+ + K^+)$-ATPase activity at 1 hour after injury,[11] provide a mechanistic rationale for using these massive doses of glucocorticoid soon after trauma. The pharmacokinetic measurements in this report provide further support for the necessity of early initiation of therapy and intensive maintenance dosing if optimal glucocorticoid tissue levels are to be achieved and maintained in the treatment of acute central nervous system trauma. Furthermore, since a single 30-mg/kg dose of methylprednisolone is virtually without harmful effects,[15] the administration of such a dose, even before a spinal injury is confirmed (perhaps at the accident site), may be warranted.

SUMMARY OF THE INVENTION

The method of this invention comprises treating stroke syndrome patients with an amount of a water soluble 21-dibasic ester of 1-dehydro-6α-methylhydrocortisone, preferably methylprednisolone sodium succinate, molar equivalent to about 60 mg/kg/day to about 100 mg/kg/day of 1-dehydro-6α-methylhydrocortisone, beginning as soon as possible following initial symptoms/signs of a stroke. Treating stroke syndrome in accordance with the subject invention alleviates and protects against irreversible brain damage during the acute stages of stroke syndrom and promotes functional recovery.

DETAILED DESCRIPTION OF THE INVENTION

In accordance with the manner and process of using the present invention, water soluble 21-dibasic esters of 1-dehydro-6α-methylhydrocortisone and their salts are administered parenterally, preferably intravenously to humans in need of such treatment to treat stroke syndrome. An especially effective compound for use in the process of this invention is 1-dehydro-6α-methylhydrocortisone 21-hemisuccinate sodium salt (6α-methylprednisolone 21-succinate sodium salt).

The water soluble 21-dibasic esters of 1-dehydro-6α-methylhydrocortisone and their salts can be prepared by methods known in the art. U.S. Pat. No. 2,897,218 discloses such a method. The essential material constituting a disclosure of how to prepare and formulate said esters and salts is incorporated here by reference from U.S. Pat. No. 2,897,218.

The water soluble 21-dibasic esters of 1-dehydro-6α-methylhydrocortisone and their salts can be formulated for use in sterile intravenous solutions by methods that are conventional in the art.

The formulation as prepared can be administered in varying dosages depending upon the weight of the human under treatment. The daily dosage ranges from an amount equivalent to about 60 mg/kg/day to about 100 mg/kg/day of 1-dehydro-6α-methylhydrocortisone is divided doses. An initial dose of from about 20 mg/kg to about 40 mg/kg, preferably from about 25 mg/kg to about 35 mg/kg, is adminstered intravenously as soon as possible following initial symptoms/signs of a stroke. The prefered regimen of administration is about 30 mg/kg administered intravenously as soon as possible following initial symptoms/signs of a stroke, a second dose of about 15 mg/kg administered intravenously about two (2) hours after the initial dose, and a 15 mg/kg intravenous dose given every six (6) hours thereafter (or alternatively a continuous intravenous infusion of 15 mg/kg over six hours) for about two to about three days.

The following Example is illustrative of the method of this invention, but is not to be construed as limiting.

EXAMPLE 1

Enough formulation containing 1-dehydro-6-methylhydrocortisone 21-hemisuccinate sodium salt, as the active ingredient, to prepare 1000 8 ml vials, each containing the equivalent of 500 mg of methylprednisolone is prepared from the following types and amounts of ingredients

| | |
|---|---:|
| 1-Dehydro-6α-methylhydrocortisone 21-hemisuccinate sodium salt (equivalent to 500 mg/vial of 1-dehydro-6α-methylhydrocortisone itself) | 663 grams |
| Sodium Biphosphate, Anhydrous | 6.4 grams |
| Dried Sodium Phosphate | 69.6 grams |
| Benzyl Alcohol | 66.8 grams |

Sterile intravenous solutions of the prepared formulations can be prepared by mixing the content of a vial with 8 ml of bacteriostatic water.

The sterile solution is administered as follows, to treat stroke syndrome in a 70-kilo/adult human.

Four vials are administered intravenously over a 10–20 minute period beginning as soon as possible following initial symptoms/signs of a stroke. Two vials are administered intravenously over a 10–20 minute period beginning two hours after administration of the initial 30 mg/kg dose and two vials are admixed with 0.5 liter of 5% dextrose in water, isotonic saline solution or 5% dextrose in isotonic saline solution and administered intravenously as a continuous intravenous infusion over six hours. The infusion is repeated every six hours for three days.

Other 21-polybasic esters of 1-dehydro-6α-methylhydrocortisone and their salts can be used to prepare formulations that can be used in the method of this invention. They include:

1-dehydro-6α-methylhydrocortisone 21-hemisuccinate phenylephrine salt 1-dehydro-6α-methylhydrocortisone 21-hemisuccinate N-methyl-glucamine salt 1-dehydro-6α-methylhydrocortisone 21-(α,β-dimethylglutamate)

1-dehydro-6α-methylhydrocortisone 21-glycolate 1-dehydro-6α-methylhydrocortisone 21-tartrate and the sodium phenylephrine and N-methyl-glucamin salts thereof.

Following the procedure of Example 1, compositions are similarly prepared substituting an amount of the foregoing compounds equivalent to 500 mg/vial of 1-dehydro-6α-methylhydrocortisone itself for the 1-dehydro-6α-methylhydrocortisone 21-hemisuccinate sodium salt of the example.

We claim:

1. A method of treating stroke syndrome which comprises administering intravenously to a human in need of such treatment, an amount of a compound selected from the group consisting of a water soluble 21-dibasic ester of 1-dehydro-6α-methylhydrocortisone and their salts, molar equivalent to from about 60 mg/kg/day to about 100 mg/kg/day of 1-dehydro-6α-methylhydrocortisone, in a pharmaceutically acceptable carrier.

2. A method according to claim 1 wherein the compound is 1-dehydro-6α-methylhydrocortisone 21-hemisuccinate sodium salt.

3. A method of treating stroke syndrome which comprises initially administering intravenously to a human in need of such treatment, an amount of a compound selected from the group consisting of a water soluble 21-dibasic ester of 1-dehydro-6α-methylhydrocortisone and their salts, molar equivalent to from about 20 mg/kg to about 40 mg/kg of 1-dehydro-6α-methylhydrocortisone, in a pharmaceutically acceptable carrier.

4. A method according to claim 3 wherein the compound is 1-dehydro-6α-methylhydrocortisone 21-hemisuccinate sodium salt.

5. The method according to claim 3 wherein the amount of the compound is molar equivalent to from about 25 mg/kg to about 35 mg/kg of 1-dehydro-6α-methylhydrocortisone.

* * * * *

UNITED STATES PATENT OFFICE
CERTIFICATE OF CORRECTION

Patent No. 4,554,271            Dated   19 November 1985

Inventor(s)   J. Mark Braughler and Edward D. Hall

It is certified that error appears in the above-identified patent and that said Letters Patent are hereby corrected as shown below:

Column 1, line 36:  "incensive" should read:  -- intensive --.

Column 2, line 11:  "weights" should read:  -- weight --.

Column 2, line 48:  "confused" should read:  -- contused --.

Column 3, lines 23-24:  "hermorrhagic" should read:  -- hemorrhagic --.

Column 5, line 48:  "syndrom" should read:  -- syndrome --.

Column 6, lines 26-27:  ""-6-methyl-hydrocortisone" should read:  -- -6-α-methylhydrocortisone --.

Column 6, line 10:  "is divided" should read:  -- in divided --.

Column 6, line 65:  "glucamine salt" should read:  -- glycamin salt --.

Column 7, line 2:  "sodium" should read:  -- sodium, --.

Signed and Sealed this

Fourteenth Day of October, 1986

[SEAL]

Attest:

DONALD J. QUIGG

Attesting Officer    Commissioner of Patents and Trademarks